United States Patent
Kubota et al.

(10) Patent No.: US 11,523,760 B2
(45) Date of Patent: Dec. 13, 2022

(54) AROUSAL STATE ESTIMATION APPARATUS AND AROUSAL STATE ESTIMATION METHOD

(71) Applicants: HONDA MOTOR CO., LTD., Tokyo (JP); KYUSHU UNIVERSITY, NATIONAL UNIVERSITY CORPORATION, Fukuoka (JP)

(72) Inventors: Tadahiro Kubota, Wako (JP); Tomohiro Imai, Wako (JP); Shigekazu Higuchi, Fukuoka (JP); Kosuke Okusa, Fukuoka (JP); Hisao Yoshida, Fukuoka (JP); Yuka Egashira, Fukuoka (JP); Yuki Nishimura, Fukuoka (JP)

(73) Assignees: HONDA MOTOR CO., LTD., Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 173 days.

(21) Appl. No.: 15/931,735

(22) Filed: May 14, 2020

(65) Prior Publication Data
US 2020/0367797 A1 Nov. 26, 2020

(30) Foreign Application Priority Data
May 21, 2019 (JP) .............................. JP2019-095167

(51) Int. Cl.
*A61B 5/16* (2006.01)
*G06F 3/01* (2006.01)
*G06K 9/62* (2022.01)

(52) U.S. Cl.
CPC .............. *A61B 5/165* (2013.01); *G06F 3/015* (2013.01); *G06F 3/017* (2013.01); *G06K 9/6232* (2013.01); *G06F 2203/011* (2013.01)

(58) Field of Classification Search
CPC .... G06F 3/015; G06F 3/017; G06F 2203/011; A61B 5/165
(Continued)

(56) References Cited

U.S. PATENT DOCUMENTS 5,676,138 A * 10/1997 Zawilinski ............. A61B 5/389
600/301
10,827,973 B1 * 11/2020 Alzamzmi ............. G16H 50/70
(Continued)

FOREIGN PATENT DOCUMENTS

JP 2010-142273 7/2010
JP 2013-013542 1/2013
(Continued)

OTHER PUBLICATIONS

Kaida, et al. "Validation of the Karolinska sleepiness scale against performance and EEG variables", Clinical NeuroPhysiology, 2006. 07, vol. 117, Issue 7, pp. 1574-1581.
(Continued)

*Primary Examiner* — Calvin C Ma
(74) *Attorney, Agent, or Firm* — Amin, Turocy & Watson, LLP

(57) ABSTRACT

An arousal state estimation apparatus includes: a feature value acquisition unit acquiring a plurality of types of feature values regarding an arousal state of a human body from physiological data obtained by measuring the human body; and an estimation unit estimating the arousal state of the human body by using a principal feature value that is some type among the plurality of types of feature values. In a case where the principal feature value is unacquirable due to a defect of the physiological data, the estimation unit estimates the arousal state of the human body by using a different type of feature value than the principal feature value among the plurality of types of feature values acquired
(Continued)

by the feature value acquisition unit instead of the unacquirable principal feature value.

8 Claims, 8 Drawing Sheets

(58) Field of Classification Search
 USPC .......................................................... 600/300
 See application file for complete search history.

(56) References Cited

U.S. PATENT DOCUMENTS

2016/0000365 A1   1/2016  Kushki et al.
2019/0373962 A1*  12/2019 Datta .................. A41D 13/1281
2019/0388695 A1*  12/2019 Dinsmoor .......... A61N 1/36062

FOREIGN PATENT DOCUMENTS

JP   2015-080624    4/2015
JP      2015-21698   11/2015
JP   2015-228970   12/2015
JP   2018-082931    5/2018

OTHER PUBLICATIONS

Japanese Office Action for Japanese Patent Application No. 2019-095167 dated Oct. 25, 2022.

* cited by examiner

FIG. 3
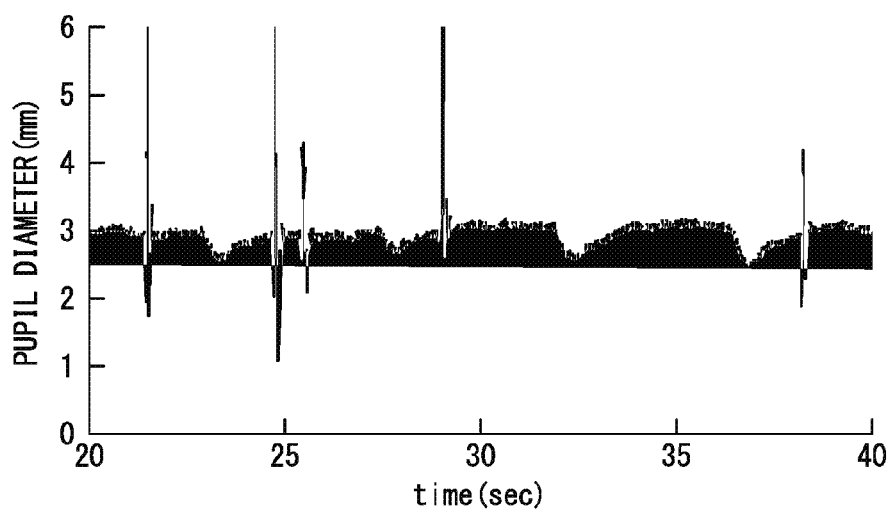
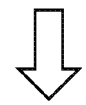
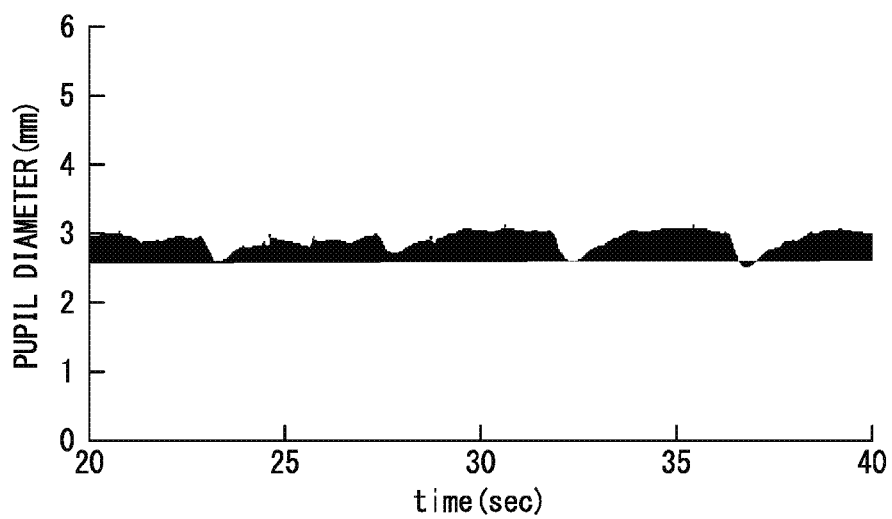

FIG. 4

| PART | NAME | FEATURE VALUE TYPE |
|---|---|---|
| SUBJECTIVE | KSS | 1 (AROUSAL)-9 (DROWSINESS) |
| ELECTROCARDIOGRAM | HR | HEART RATE PER MINUTE($1/RR_i$) |
| | CSI | L/T OF $RR_i/RR_{i+1}$ PLOT |
| | CVI | $\log_{10}(L \times T)$ OF $RR_i/RR_{i+1}$ PLOT |
| | HF/(LF+HF) | RATIO BETWEEN LF (0.15 Hz <) AND HF (0.15 Hz >) |
| RESPIRATION | RESP | SINGLE-TEST AVERAGE RESPIRATION INTERVAL |
| PULSE WAVE | PULSE | SINGLE-TEST AVERAGE PEAK AMPLITUDE |
| SKIN ACTION POTENTIAL | SCR | SINGLE-TEST AVERAGE SURFACE POTENTIAL |
| BLINK | BLINK | SINGLE-TEST NUMBER-OF-BLINKS (EYE POTENTIAL) |
| PUPIL DIAMETER | PUPIL | SINGLE-TEST AVERAGE PUPIL DIAMETER |
| HEAD MOVEMENT | HEAD_X, Y, Z | SINGLE-TEST AVERAGE HEAD MOVEMENT AMOUNT (ACCELERATION) |

FIG. 5

| | VAS | KSS | HR | CVI | CSI | HF/(LF+HF) | PULSE | RESP | SCR | BLINK | PUPIL | HEAD_X | HEAD_Y | HEAD_Z |
|---|---|---|---|---|---|---|---|---|---|---|---|---|---|---|
| VAS | 1 | 0.98 | 0.23 | 0.02 | 0.26 | -0.32 | 0.09 | -0.03 | -0.16 | 0.01 | -0.46 | 0.2 | -0.17 | 0.09 |
| KSS | 0.98 | 1 | 0.24 | 0.02 | 0.27 | -0.32 | 0.1 | -0.01 | -0.16 | 0.02 | -0.47 | 0.2 | -0.15 | 0.07 |
| HR | 0.23 | 0.24 | 1 | -0.38 | 0.45 | -0.36 | -0.1 | 0.01 | 0.04 | -0.04 | -0.07 | 0.05 | 0.11 | -0.11 |
| CVI | 0.02 | 0.02 | -0.38 | 1 | 0.26 | -0.2 | 0.07 | 0.19 | 0.1 | 0.13 | 0.02 | 0.11 | -0.22 | 0.15 |
| CSI | 0.26 | 0.27 | 0.45 | 0.26 | 1 | -0.61 | -0.03 | 0.14 | 0.06 | 0.08 | -0.1 | 0.16 | -0.06 | -0.03 |
| HF/(LF+HF) | -0.32 | -0.32 | -0.36 | -0.2 | -0.61 | 1 | 0.04 | -0.16 | -0.01 | -0.06 | 0.2 | -0.13 | 0.1 | -0.04 |
| PULSE | 0.09 | 0.1 | -0.1 | 0.07 | -0.03 | 0.04 | 1 | -0.04 | 0.01 | 0.09 | -0.1 | 0 | -0.05 | 0.02 |
| RESP | -0.03 | -0.01 | 0.01 | 0.19 | 0.14 | -0.16 | -0.04 | 1 | 0.13 | 0.12 | 0.01 | 0.05 | -0.03 | 0.01 |
| SCR | -0.16 | -0.16 | 0.04 | 0.1 | 0.06 | -0.01 | 0.01 | 0.13 | 1 | 0.11 | 0.22 | 0.03 | -0.02 | 0.01 |
| BLINK | 0.01 | 0.02 | -0.04 | 0.13 | 0.08 | -0.06 | 0.09 | 0.12 | 0.11 | 1 | 0.06 | 0.08 | -0.04 | -0.01 |
| PUPIL | -0.46 | -0.47 | -0.07 | 0.02 | -0.1 | 0.2 | -0.1 | 0.01 | 0.22 | 0.06 | 1 | -0.16 | 0.06 | -0.03 |
| HEAD_X | 0.2 | 0.2 | 0.05 | 0.11 | 0.16 | -0.13 | 0 | 0.05 | 0.03 | 0.08 | -0.16 | 1 | -0.58 | 0.05 |
| HEAD_Y | -0.17 | -0.15 | 0.11 | -0.22 | -0.06 | 0.1 | -0.05 | -0.03 | -0.02 | -0.04 | 0.06 | -0.58 | 1 | -0.71 |
| HEAD_Z | 0.09 | 0.07 | -0.11 | 0.15 | -0.03 | -0.04 | 0.02 | 0.01 | 0.01 | -0.01 | -0.03 | 0.05 | -0.71 | 1 |

AROUSAL STATE ESTIMATION APPARATUS AND AROUSAL STATE ESTIMATION METHOD

CROSS-REFERENCE TO RELATED APPLICATION

Priority is claimed on Japanese Patent Application No. 2019-095167, filed on May 21, 2019, the contents of which are incorporated herein by reference.

BACKGROUND

Field of the Invention

The present invention relates to an arousal state estimation apparatus and an arousal state estimation method.

Background

There is a technique of determining an arousal state on the basis of physiological data of the human body (for example, refer to Japanese Unexamined Patent Application, First Publication No. 2013-13542). In this technique, low arousal, that is, drowsiness is predicted on the basis of a heartbeat interval and a respiratory periodicity component obtained from state detection data for the human body, and time-series changes thereof.

SUMMARY

In the technique of the related art, in a case where some physiological data of the human body used for prediction is defective, there is a problem in that an arousal state cannot be accurately predicted in a period in which the data is defective.

An aspect of the present invention is directed to providing an arousal state estimation apparatus and an arousal state estimation method capable of predicting an arousal state even in a period in which some physiological data of the human body used for prediction is defective.

According to a first aspect of the present invention, an arousal state estimation apparatus is provided including a feature value acquisition unit acquiring a plurality of types of feature values regarding an arousal state of a human body from physiological data obtained by measuring the human body; and an estimation unit estimating the arousal state of the human body by using a principal feature value that is some type among the plurality of types of feature values, in which, in a case where the principal feature value is unacquirable due to a defect of the physiological data, the estimation unit estimates the arousal state of the human body by using a different type of feature value than the principal feature value among the plurality of types of feature values acquired by the feature value acquisition unit instead of the unacquirable principal feature value.

According to a second aspect of the present invention, in the arousal state estimation apparatus according to the first aspect, the estimation unit may use a type of feature value having a high correlation with the unacquirable principal feature value instead of the unacquirable principal feature value.

According to a third aspect of the present invention, in the arousal state estimation apparatus according to the first or second aspect, the physiological data may include a measurement result of a heart, respiration, a fingertip pulse, a skin resistance, blinking, a pupil, or head movement.

According to a fourth aspect of the present invention, in the arousal state estimation apparatus according to any one of the first to third aspects, in a case where there is a defect in the physiological data, the feature amount acquisition unit may supplement the physiological data at a timing related to the defect based on the physiological data obtained at another timing.

According to a fifth aspect of the present invention, an arousal state estimation method is provided including acquiring a plurality of types of feature values regarding an arousal state of a human body from physiological data obtained by measuring the human body; estimating the arousal state of the human body by using a principal feature value that is some type among the plurality of types of feature values; and estimating, in a case where the principal feature value is unacquirable due to a defect of the physiological data, the arousal state of the human body by using a different type of feature value than the principal feature value among the plurality of types of acquired feature values instead of the unacquirable principal feature value.

According to the first or fifth aspect, it is possible to continuously predict an arousal state even in a period in which a part of physiological data of a human body used to predict the arousal state is defective.

According to the second aspect, it is possible to continuously predict an arousal state without considerably reducing the accuracy of prediction even in a period in which part of physiological data of a human body used to predict the arousal state is defective.

According to the third aspect, a feature value highly associated with an arousal state can be obtained, and thus it is possible to predict the arousal state with high accuracy.

According to the fourth aspect, even in a case where physiological data used to obtain a principal feature value is temporarily defective, the principal feature value can be obtained by supplementing the physiological data, and thus it is possible to continuously predict an arousal state with high accuracy.

BRIEF DESCRIPTION OF THE DRAWINGS

FIG. 3 is a diagram illustrating an example of supplementation of physiological data according to the embodiment.

FIG. 4 is a diagram illustrating physiological data and feature values according to the embodiment.

FIG. 5 is a diagram illustrating a correlation between a feature value and the degree of arousal that can be used for an arousal state estimation model according to the embodiment.

DESCRIPTION OF EMBODIMENTS

Hereinafter, an embodiment of the present invention will be described with reference to the drawings.

Figure 1:
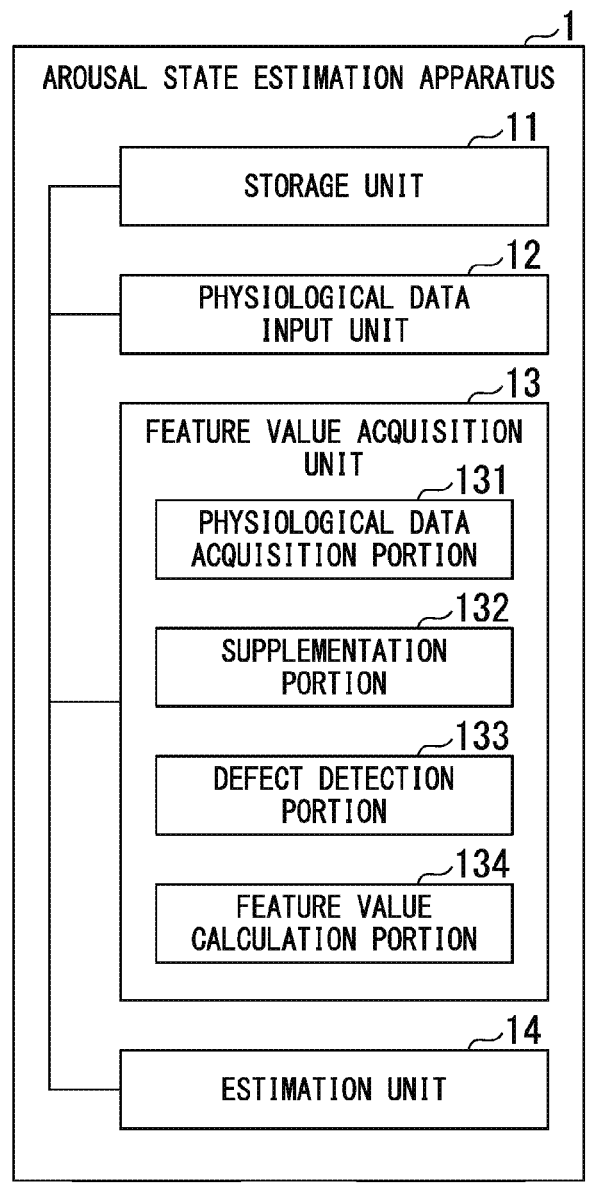
FIG. 1 is a block diagram illustrating a configuration example of an arousal state estimation apparatus according to an embodiment of the present invention.

FIG. 1 is a block diagram illustrating a configuration example of an arousal state estimation apparatus 1 according to the present embodiment. The arousal state estimation apparatus 1 includes a storage unit 11, a physiological data input unit 12, a feature value acquisition unit 13, and an estimation unit 14. The constituent elements are realized, for example, by a hardware processor such as a central processing unit (CPU) executing a program (software). Some or all of the constituent elements may be realized by hardware (a circuit portion; including a circuitry) such as a large scale integration (LSI), an application specific integrated circuit (ASIC), a field-programmable gate array (FPGA), or a graphics processing unit (GPU), and may be realized by software and hardware in cooperation. The program may be stored in advance in a storage device (a storage device provided with a non-transitory storage medium) such as a hard disk drive (HDD) or a flash memory, or may be stored in an attachable and detachable storage medium (non-transitory storage medium) such as a DVD or a CD-ROM and be installed when the storage medium is attached to a drive device.

The storage unit 11 stores various pieces of data. The storage unit 11 stores m (where m is an integer of 1 or greater) types of physiological data, n (where n is an integer of 2 or greater) types of feature values, and an arousal state estimation model. The physiological data is physiological data obtained by measuring a person who is an arousal state estimation target. The feature value is digitized information of a feature regarding an arousal state of the human body and is obtained from the physiological data. The physiological data may be the feature value. For example, the feature value may be obtained from the physiological data indicating a measurement result of the heart, respiration, a fingertip pulse, a skin resistance, blinking, a pupil, or head movement. The arousal state estimation model is an equation for calculating the degree of arousal by using k (where k is an integer of 1 or greater, and k<n) types of some feature values greatly contributing to determination of an arousal state among the n types of feature values. The degree of arousal is a quantified value representing an arousal state of the human body. The k types of feature values greatly contributing to determination of an arousal state will be referred to as principal feature values. The storage unit 11 further stores a substitute feature value that is a feature value used when each principal feature value cannot be acquired, and substitute calculation information indicating model change information when the substitute feature value is used. The model change information indicates a change of the arousal state estimation model.

For example, the arousal state estimation model is an equation for calculating the degree of arousal Y according to the following Equation (1) by using three (k=3) types of principal feature values $a_1$, $b_1$, and $c_1$ among six (m=6) types of feature values $a_1$, $a_2$, $b_1$, $b_2$, $c_1$, and $c_2$. Here, $\alpha_0$, $\beta_0$, and $\gamma_0$ are coefficients.

$$\text{Degree of arousal } Y = \alpha_0 a_1 + \beta_0 b_0 + \gamma_0 c_1 \qquad (1)$$

The substitute calculation information includes information indicating that a substitute feature value of the principal feature value $a_1$ is the feature value $b_2$, and model change information indicating that the coefficient $\alpha_0$ is changed to the coefficient $\alpha_1$ in a case where the substitute feature value $b_2$ is used.

Therefore, in a case where the principal feature value $a_1$ cannot be obtained, and the substitute feature value $b_2$ is used, the arousal state estimation model is the following Equation (2).

$$\text{Degree of arousal } Y = \alpha_1 b_2 + \beta_0 b_1 + \gamma_0 c_1 \qquad (2)$$

The substitute calculation information may include a correspondence between a single principal feature value and a plurality of substitute feature values in a prioritized order. The substitute feature value may be a combination of a plurality of feature values. For example, in a case where a combination of the feature values $b_2$ and $c_2$ is used as a substitute feature value when the principal feature value $a_1$ cannot be obtained, the model change information may indicate that the term "$\alpha_0 a_1$" in Equation (1) is replaced with "$\alpha_{11} b_2 + \alpha_{12} c_2$" (where $\alpha_{11}$ and $\alpha_{12}$ are coefficients). The principal feature value and the substitute feature value thereof may be feature values obtained from different pieces of physiological data, but may be feature values obtained from the same physiological data.

The physiological data input unit 12 receives m types of time-series physiological data from an external device such as a measurement device and stores the physiological data into the storage unit 11. The feature value acquisition unit 13 acquires n types of feature values on the basis of the m types of physiological data stored in the storage unit 11. The feature value acquisition unit 13 includes a physiological data acquisition portion 131, a supplementation portion 132, a defect detection portion 133, and a feature value calculation portion 134. The physiological data acquisition portion 131 acquires physiological data in a section used to acquire a feature value by using each of the m types of time-series physiological data stored in the storage unit 11. The section is a temporal length represented by a start timing and an end timing. The supplementation portion 132 supplements a value of defective physiological data in a section used to acquire a feature value on the basis of a value of physiological data at a timing at which there are no defects. The defect detection portion 133 detects whether or not there is a defect in each piece of physiological data subjected to a supplementation process. The defect detection portion 133 notifies the feature value calculation portion 134 of the type of defective physiological data. The feature value calculation portion 134 acquires a feature value from physiological data with no defect and outputs the feature value to the estimation unit 14. The feature value calculation portion 134 may acquire a plurality of types of feature values from one type of physiological data and may acquire one type of feature value from a plurality of types of physiological data.

Each type of feature value is a normalized value in the same numerical range. In a case where the type of defective physiological data is received from the defect detection portion 133, the feature value calculation portion 134 notifies the estimation unit 14 of the type of feature value that cannot be acquired due to the type of defective physiological data.

The estimation unit 14 reads the arousal state estimation model from the storage unit 11. At a timing at which there are no defects in any of the k types of principal feature values, the estimation unit 14 assigns the k types of principal feature values to values of variables of the arousal state estimation model, to calculate the degree of arousal. At a timing at which there is a notification that at least one of the k types of principal feature values is defective, the estimation unit 14 selects a substitute feature value of which a priority is highest and which is not defective from among substitute feature values of the defective principal feature value on the basis of the substitute calculation information. The estimation unit 14 changes the arousal state estimation model on the basis of model change information corresponding to the selected substitute feature value. The estimation unit 14 assigns the selected substitute feature value and the principal feature value with no defect to values of variables of the changed arousal state estimation model, to calculate the degree of arousal. The estimation unit 14 outputs the calculated degree of arousal as an estimation result. The output may be, for example, display on a display, may be output of data to an external device, and may be output using a voice.

The arousal state estimation apparatus 1 may be implemented by a plurality of computer apparatuses connected to a network. In this case, each functional unit of the arousal state estimation apparatus 1 may be realized by any of the plurality of computer apparatuses. A single functional unit may be realized by the plurality of computer apparatuses. Distributed processes and integrated processes may be performed by using the plurality of computer apparatuses.

Figure 2:
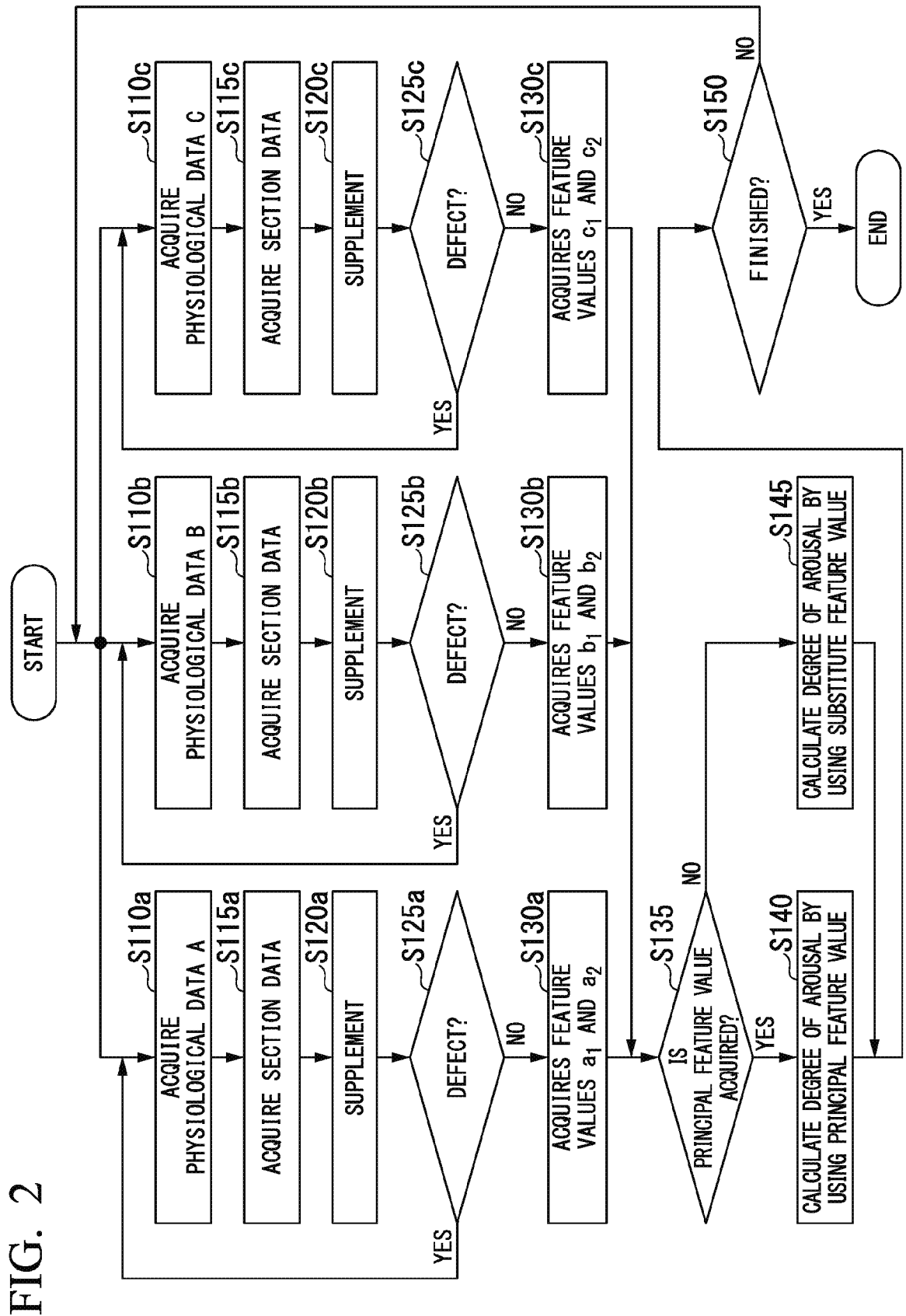
FIG. 2 is a flowchart illustrating an example of a process in the arousal state estimation apparatus according to the embodiment.

FIG. 2 is a flowchart illustrating an example of a process in the arousal state estimation apparatus 1. Hereinafter, as an example, a description will be made of a case where physiological data is three (m=3) types of physiological data A, B, and C, feature values are six (n=6) types of feature values including feature values $a_1$ and $a_2$ obtained from the physiological data A, feature values $b_1$ and $b_2$ obtained from the physiological data B, and feature values $c_1$ and $c_2$ obtained from the physiological data C, and principal feature values are three (k=3) types of feature values $a_1$, $b_1$, and $c_1$.

The physiological data input unit 12 sequentially receives the physiological data A from an external device and stores the physiological data A into the storage unit 11 (step S110a). The physiological data acquisition portion 131 extracts the physiological data A in a section from the latest time point to a time point corresponding to a predetermined time before the latest time, from the time-series physiological data A stored in the storage unit 11 (step S115a). This section will be referred to as an extraction target section.

The extraction target section is a time section of the physiological data A required to calculate the feature values $a_1$ and $a_2$.

In a case where there is a defect in the physiological data A, the supplementation portion 132 performs a supplementation process. The supplementation portion 132 determines that a section in which the physiological data A cannot be acquired in the extraction target section is a defective section. The supplementation portion 132 determines whether or not the physiological data A in the extraction target section has a normally detected value and determines that a section in which the physiological data A can be acquired but the physiological data A does not have a normally detected value is a defective section. The supplementation portion 132 supplements a value of the physiological data A in the defective section by using a section of the physiological data A of which a normal value can be acquired in the physiological data A in the extraction target section (step S120a). An example of supplementation will be described later with reference to FIG. 3. The supplementation portion 132 may perform supplementation by further using the physiological data A in a section before the extraction target section. In a case where the physiological data A is defective in a section of a predetermined length or more in the extraction target section, the supplementation portion 132 determines that supplementation is not possible and does not perform a supplementation process.

The defect detection portion 133 determines whether or not there is a defect in the physiological data A subjected to the supplementation process in the extraction target section (step S125a). In a case where it is determined that there is a defect (step S125a: YES), the defect detection portion 133 outputs the defect of the physiological data A to the feature value calculation portion 134. The feature value calculation portion 134 stores information indicating that the feature values $a_1$ and $a_2$ are defective into the storage unit 11 in correlation with timing information indicated by the extraction target section. The arousal state estimation apparatus 1 returns to step S110a and acquires the new physiological data A.

On the other hand, in a case where it is determined that there are no defects (step S125a: NO), the defect detection portion 133 outputs the physiological data A to the feature value calculation portion 134. Even in a case where there is a defective section in part of the physiological data A after being supplemented, when the defective section is equal to or shorter than a section that does not influence calculation of a feature value, the defect detection portion 133 may determine that there are no defects. The feature value calculation portion 134 acquires the feature values $a_1$ and $a_2$ from the physiological data A after being supplemented (step S130a). The feature value calculation portion 134 stores the acquired feature values $a_1$ and $a_2$ into the storage unit 11 in correlation with the timing information indicated by the extraction target section.

The arousal state estimation apparatus 1 performs the same processes as those in step S110a to step S130a on the physiological data B and C. In other words, the physiological data input unit 12 sequentially receives the physiological data B and C from the external device and stores the physiological data B and C into the storage unit 11 (step S110b and step S110c). The physiological data acquisition portion 131 extracts the physiological data B and C in extraction target sections (step S115b and step S115c). In a case where there are defects in the physiological data B and C, the supplementation portion 132 performs a supplementation process (step S120b and step S120c). The defect detection portion 133 determines whether or not there are defects in the physiological data B and C subjected to the supplementation process in the extraction target sections (step S125b and step S125c).

In a case where the defect detection portion 133 determines that there is a defect in the physiological data B (step S125b: YES), the feature value calculation portion 134 stores information indicating that the feature values $b_1$ and $b_2$ are defective into the storage unit 11 in correlation with timing information indicated by the extraction target section. The arousal state estimation apparatus 1 returns to step S110b. On the other hand, in a case where the defect detection portion 133 determines that there are no defects in the physiological data B (step S125b: NO), the feature value calculation portion 134 acquires the feature values $b_1$ and $b_2$ from the supplemented physiological data B and stores the feature values $b_1$ and $b_2$ into the storage unit 11 in correlation with the timing information indicated by the extraction target section (step S130b). In a case where the defect detection portion 133 determines that there is a defect in the physiological data C (step S125c: YES), the feature value calculation portion 134 stores information indicating that the feature values $c_1$ and $c_2$ are defective into the storage unit 11 in correlation with timing information indicated by the extraction target section. The arousal state estimation apparatus 1 returns to step S110c. On the other hand, in a case where the defect detection portion 133 determines that there are no defects in the physiological data C (step S125c: NO), the feature value calculation portion 134 acquires the feature values $c_1$ and $c_2$ from the supplemented physiological data C and stores the feature values $c_1$ and $c_2$ into the storage unit 11 in correlation with the timing information indicated by the extraction target section (step S130c).

The estimation unit 14 refers to the storage unit 11 and determines whether or not all of the feature values $a_1$, $b_1$, and $c_1$ that are principal feature values can be acquired at a timing used to calculate the degree of arousal (step S135). In a case where it is determined that all of the principal feature values can be acquired (step S135: YES), the estimation unit 14 determines that, for example, the arousal state estimation model of Equation (1) will be used. The estimation unit 14 assigns the feature values $a_1$, $b_1$, and $c_1$ at the timing used to calculate the degree of arousal to values of the variables of the arousal state estimation model, to calculate the degree of arousal Y (step S140). The estimation unit 14 outputs the calculated degree of arousal.

In a case where it is determined that there is a feature value that cannot be acquired among the feature values $a_1$, $b_1$, and $c_1$ that are principal feature values (step S135: NO), the estimation unit 14 selects a substitute feature value. Specifically, the estimation unit 14 selects substitute feature values that can be acquired at the timing used to calculate the degree of arousal from among substitute feature values stored in substitute calculation information in correspondence with the principal feature value that cannot be acquired, in a decreasing order from the substitute feature value having the highest correlation with the principal feature value among the substitute feature values that can be acquired. The correlation is calculated in advance, for example, by using a correlation coefficient based on regression analysis (FIG. 5 which will be described later) or an eigenvector azimuth (FIG. 8 which will be described later) based on principal component analysis (PCA). Therefore, a priority order of each of a plurality of substitute feature values set to be correlated with a single principal feature value in the substitute calculation information can be made to be a value based on a correlation. The estimation unit 14 reads model change information corresponding to a principal feature value that cannot be acquired and a selected substitute feature value from the substitute calculation information. The estimation unit 14 assigns a principal feature value and a substitute feature value acquired at a timing used to calculate the degree of arousal to values of variables of an arousal state estimation model changed by using the model change information, to calculate the degree of arousal Y (step S145). The estimation unit 14 outputs the calculated degree of arousal.

For example, in a case where it is determined that the principal feature value $a_1$ cannot be acquired among the principal feature values $a_1$, $b_1$, and $c_1$, the estimation unit 14 selects the feature value $b_2$ as a substitute feature value. The estimation unit 14 changes the arousal state estimation model of the above Equation (1) to the arousal state estimation model of the above Equation (2) according to the model change information. The estimation unit assigns the principal feature values $b_1$ and $c_1$ that can be acquired and the substitute feature value $b_2$ to the arousal state estimation model of Equation (2), to calculate the degree of arousal Y.

In a case where the estimation unit 14 determines whether or not the process is finished (step S150: NO) after the process in step S140 or step S145, the arousal state estimation apparatus 1 cyclically and repeatedly performs the processes from steps S110a, S110b, and S110c. The estimation unit 14 determines that the process is finished in a case where a finishing instruction is input or a preset finishing time comes (step S150: YES) and finishes the process.

A description will be made of an example of a process of detecting a defect of physiological data before the supplementation portion 132 supplements the physiological data in steps S120a, S120b, and S120c. The supplementation portion 132 performs (process 1) first-order differentiation and (process 2) acquisition of the variance σ of primary analysis data on physiological data in an extraction target section. In a case where a result of the process 1 diverges (a slope is equal to or more than a threshold value), the supplementation portion 132 determines that data is discontinuous, that is, there is a defect. This is because physiological data generally has continuity. For example, in a case where the gaze pupil jumps, a data defect is detected in this stage. The supplementation portion 132 determines a data defect on the basis of a value of the variance σ obtained through the process 2. For example, in a case where a pulse amplitude is acquired, a variance of 25 pulse amplitudes at an interval of about 0.7 seconds is obtained from physiological data for 16 seconds. The supplementation portion 132 detects a pulse amplitude exceeding 4σ among the pulse amplitudes as an abnormal value (defect). In a case where the entire extraction target section is abnormal, the supplementation portion 132 performs determination by referring to a value of the variance α calculated and accumulated in the past. An average value changes depending on situations, and thus a variance is appropriate for determining a defect.

FIG. 3 is a diagram illustrating an example of supplementation of physiological data. FIG. 3(a) illustrates time-series physiological data indicating a pupil diameter (PUPIL) stored in the storage unit 11. It is supposed that a defect of physiological data indicating a pupil diameter is generated by causes such as occlusion of the eyeball due to blinking, a loss of sight due to rapid change in ambient light, and an internal processing error of a measuring instrument. For example, in a case of occlusion of the eyeball due to blinking, an abnormal value of about 0.1 seconds is detected. However, a pupil diameter may be assumed to be maintained during that time. Thus, a defect of physiological data indicating a pupil diameter can be supplemented by using occlusion of the eyeball due to blinking through the following process.

First, the supplementation portion 132 extracts only a measured value equal to or less than 10 Hz by using a low-pass filter. As the low-pass filter, a finite impulse response (FIR) filter may be used. Next, the supplementation portion 132 calculates a time difference by sampling the measured value at a predetermined sampling frequency (for example, 60 Hz). In a case where the time difference is equal to or more than a threshold value (for example, 0.1 mm), the supplementation portion 132 determines the measured value as being noise. The supplementation portion 132 removes a noise section, and linearly interpolates the removed section. Finally, the supplementation portion 132 smooths time-series pupil diameters according to a 5-point movement average. FIG. 3(b) illustrates time-series physiological data indicating a pupil diameter subjected to supplementation according to the procedure.

Also in defects of other physiological data, data can be supplemented without losing a feature by using abnormal value determination and a supplementation algorithm together. Any existing method such as a straight line or a spline curve may be applied to the supplementation. The periodicity may be used, but caution is required because the periodicity may change the degree of arousal. In a case where preceding and following sections have the same cycle, the periodicity may be applied. However, in a case where physiological data is defective in the entire section, the supplementation portion 132 determines that supplementation is not possible, and the arousal state estimation apparatus 1 acquires physiological data at the next timing as illustrated in the process flow of FIG. 2.

Next, a description will be made of an application example of the arousal state estimation apparatus 1.

First, for 20 adult males aged 22 to 24, an electrocardiogram, a respiration, a fingertip pulse, a skin conductance, a blink, a pupil diameter, and head movement were acquired, and an arousal test was performed according to the PVT task.

The PVT task is disclosed in, for example, the document "K. Kaida et al., "Validation of the Karolinska sleepiness scale against performance and EEG variables", Clinical NeuroPhysiology, July 2006, Volume 117, Issue 7:1574 to 1581". After the PVT, subjective evaluation of the Karolinska sleepiness scale (KSS) and the visual analog scale (VAS) was performed on the subjects. Twenty-four tests were performed to be divided into two, and a sufficient break was put therebetween.

FIG. 4 is a diagram showing physiological data and feature values. The table of FIG. 4 shows a part serving as a measurement target of physiological data, the type (name) of feature value and a content of the feature value obtained from physiological data, and a physiological activity typified by the feature value. However, the KSS is used not as a feature value but as the degree of arousal. The KSS represents an arousal state in a range from 1 (arousal) to 9 (drowsiness) according to a person's subjective evaluation.

A heart rate (HR), a cardiac sympathetic index (CSI), a cardiac vagal index (CVI), and HF/(LF+HF) are obtained from physiological data indicating an electrocardiogram. The HR is a heart rate per minute, and is calculated by $(1/RR_i)$. RR indicates an interval between an R wave and an R wave. The R wave is a sharp peak in the electrocardiogram. The subscript i indicates an i-th value. When a major axis component and a minor axis component of an ellipse corresponding to an elliptical distribution obtained by performing Lorentz plot analysis on $RR_i$ and $RR_{i+1}$ consecutively measured are respectively indicated by L and T, the CSI is L/T, and the CVI is $Log_{10}(L \times T)$. The HF represents a high frequency component, and the LF represents a low frequency component.

A single-test average respiration interval RESP is obtained from physiological data indicating a respiration. A single-test average peak amplitude PULSE is obtained from physiological data indicating a pulse wave. A single-test average surface potential SCR is obtained from physiological data indicating a skin action potential. A single-test number-of-blinks BLINK is obtained from physiological data indicating a blink. A single-test average pupil diameter PUPIL is obtained from physiological data indicating a pupil diameter. HEAD_X,Y,Z in which a single-test average head movement amount is represented by XYZ coordinates is obtained from physiological data indicating head movement.

In the present embodiment, for each subject, each feature value was normalized to 1 to 0 between the maximum value and the minimum value.

FIG. 5 is a diagram illustrating a correlation between a feature value and the degree of arousal used for the arousal state estimation model.

FIG. 5 illustrates results of calculating a correlation between a feature value and the degree of arousal illustrated in FIG. 4 on the basis of a result obtained through an arousal test. The degree of arousal is the VAS and the KSS. It can be seen from FIG. 5 that a correlation with the degree of arousal is high in an order of the feature values PUPIL, HF/(LF+HF), HR, HEAD_X,Y,Z, and SCR. Therefore, it is determined that the feature values contribute to estimation of the KSS in the order thereof. In a case where the feature value PUPIL having the greatest contribution is defective, it is determined that SCR, HF/(LF+HF), and HEAD_X having a high correlation with the feature value PUPIL can be used as substitutes. Such classification may be similarly determined by using not only a correlation but also a mechanical separator.

On the basis of the above result, the following Equation (3) is obtained as an evaluation equation for the degree of arousal Y obtained through multiple regression.

$$Y=\alpha_0 PUPIL+\beta_0 CSI+\gamma_0 PULSE \quad (3)$$

The arousal state estimation apparatus 1 uses Equation (3) as an arousal state estimation model. A loss of a feature value serving as a principal factor considerably reduces estimation accuracy in a time section requiring estimation. A short-term defect can be supplemented as described with reference to FIG. 3. However, in a case where Equation (3) is used without being changed even when a vacant feature value is obtained without supplementation, a greatly different state may be estimated. Therefore, in a case where the feature value PUPIL is defective, as illustrated in FIG. 4, HF/(LF+HF) or SCR having a high correlation with the feature value PUPIL is used as a substitute feature value. Equation (4) is an equation obtained through replacement with the feature value SCR.

$$Y=\alpha_1 SCR+\beta_0 CSI+\gamma_0 PULSE \quad (4)$$

Values of the coefficients $\alpha_0$, $\alpha_1$, $\beta_0$, and $\gamma_0$ are determined by using, for learning data, a result or the like of performing the arousal test or a result or the like of performing a separate arousal test. The respective feature values are normalized values, and thus the coefficient $\alpha_1$ may be the same as the coefficient $\alpha_0$.

(a) In a case where there is a feature value having a high correlation (positive or negative) through regression analysis as illustrated in FIG. 5, and (b) in a case where there is a feature value matching (close to) an azimuth of a feature value eigenvector through PCA, a principal feature value may be replaced with the feature values. In the PCA, generally, an eigenvector norm of a feature value having great contribution and serving as a principal feature value is largest, and a feature value having an eigenvector norm smaller than that is used as a substitute feature value.

For a feature value of which there is no candidate according to (a) or (b), a substitute feature value cannot be defined. In a case where a principal feature value is defective, it is considered that physiological data from which the principal feature value is obtained is defective, and thus other feature values obtained from the same physiological data as that of the principal feature value cannot be used as substitute feature values. Thus, a separate feature value obtained from different physiological data may be preferably used as a substitute feature value. Since each feature value has different information such as a sympathetic origin, a parasympathetic origin, and a vagus nerve origin, components that replace other feature values can be obtained. As the number of types of physiological data to be acquired is increased, the time and effort are increased in a case where the number of apparatuses for acquiring physiological data is increased, but a possibility of substitution is improved such that a risk of loss of a feature value can be reduced.

An arousal state estimation model and substitute calculation information may be generated by using learning data obtained for a plurality of persons, but estimation accuracy can be further improved by generating the arousal state estimation model and the substitute calculation information by using learning data for each person. In this case, the arousal state estimation model and the substitute calculation information generated for each person are stored in the storage unit 11.

The arousal state estimation apparatus 1 receives input of identification information of an arousal state estimation target person and performs a process by using an arousal state estimation model and substitute calculation information identified by the input identification information.

Figure 6:
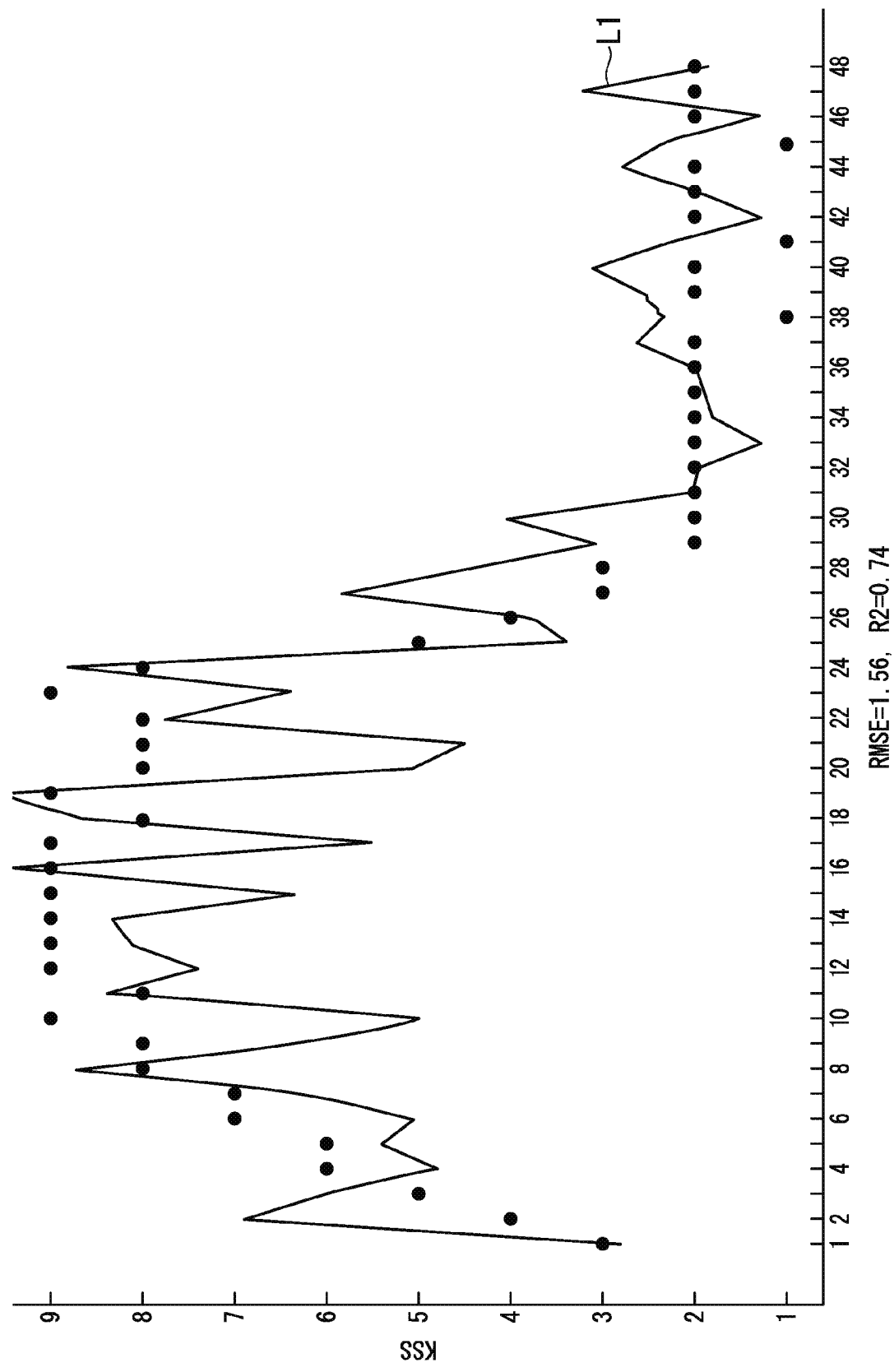
FIG. 6 is a diagram illustrating an evaluation result of the arousal state estimation model according to the embodiment.
Figure 7:
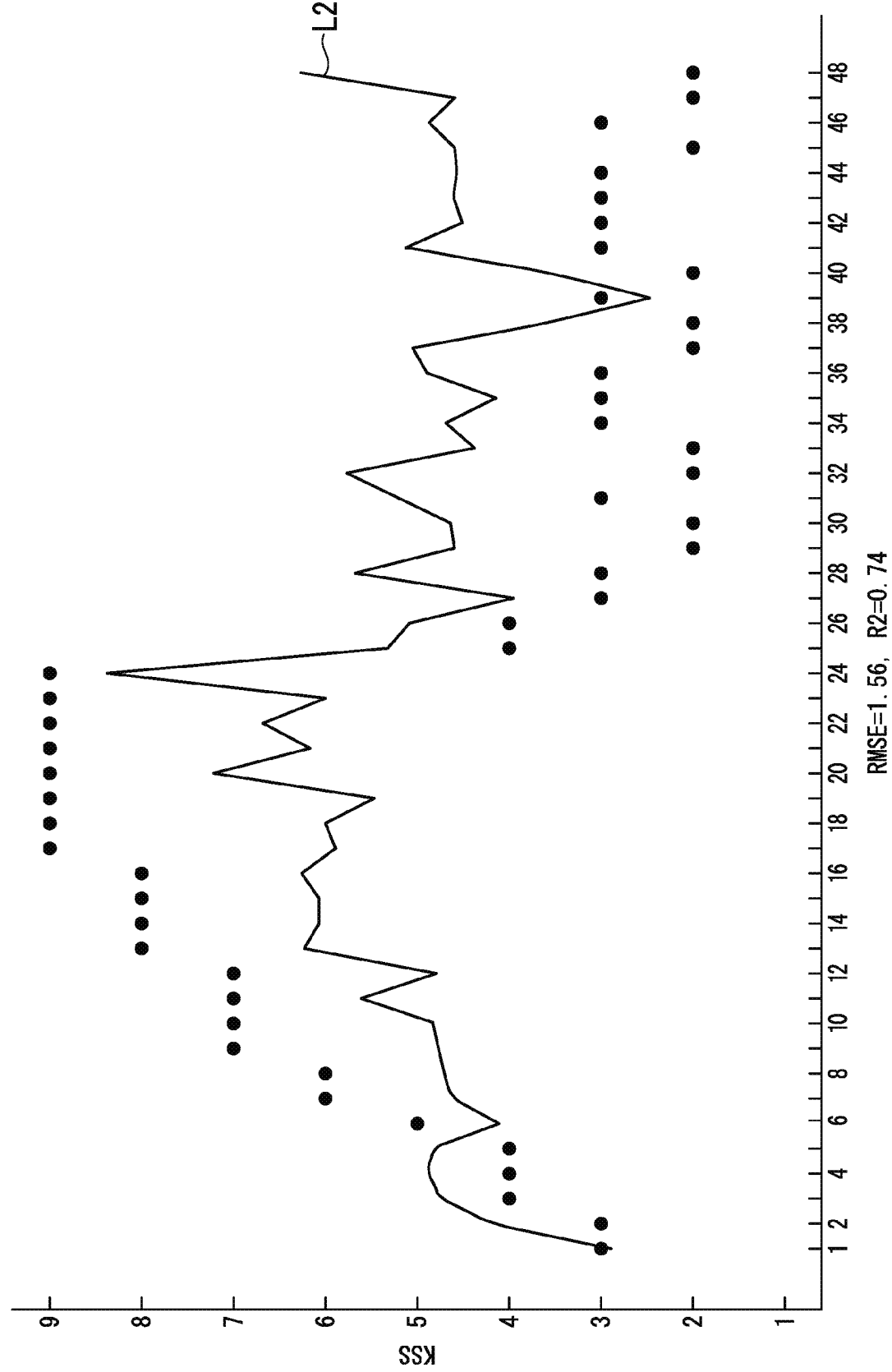
FIG. 7 is a diagram illustrating an evaluation result of the arousal state estimation model according to the embodiment.

FIGS. 6 and 7 are diagrams illustrating evaluation results of learned arousal state estimation models. FIG. 6 shows the degree of arousal Y calculated by assigning feature values acquired from physiological data in a measured new section to the arousal state estimation model represented by Equation (3), and a subjective KSS of a subject. FIG. 7 shows the degree of arousal Y calculated by assigning feature values acquired from physiological data in a measured new section to the arousal state estimation model represented by Equation (4), and a subjective KSS of a subject. A black mark indicates a value of the subjective KSS, and lines of the reference signs L1 and L2 indicate the degree of arousal Y estimated on the basis of physiological data by using the arousal state estimation models. Such determination may be similarly evaluated by using a random forest, a decision tree, or support vector regression (SVR).

According to FIG. 6, it can be seen that the degree of arousal Y estimated by using Equation (3) has a tendency similar to that of the subjective KSS. A root mean square error (RMSE) is 1.56, and a decision coefficient $R^2$ is 0.74. According to FIG. 7, the accuracy is slightly lower than in FIG. 6 in a state of being closer to KSS=9, but it can be seen that the degree of arousal Y estimated by using Equation (4) has a tendency similar to that of the subjective KSS. The RMSE is 2.11, and the decision coefficient $R^2$ is 0.43.

In the evaluation tests shown in FIGS. 6 and 7, values of the coefficients of Equations (3) and (4) were not changed. In other words, the coefficient $\alpha_0$ is the same as the coefficient $\alpha_1$. Thus, in a case where Equation (4) is used, the decision coefficient $R^2$ representing prediction accuracy is reduced. In a case where the coefficient $\alpha_1$ is corrected, values may be determined as follows. For example, in FIG. 5, in a case of linear regression, when the substitute feature value SCR is used due to a defect of the feature value PUPIL, coefficient $\alpha_1$ is set to $(0.22/0.16)\alpha_0$ by using correlation values between SCR, and VAS and PUPIL.

Figure 8:
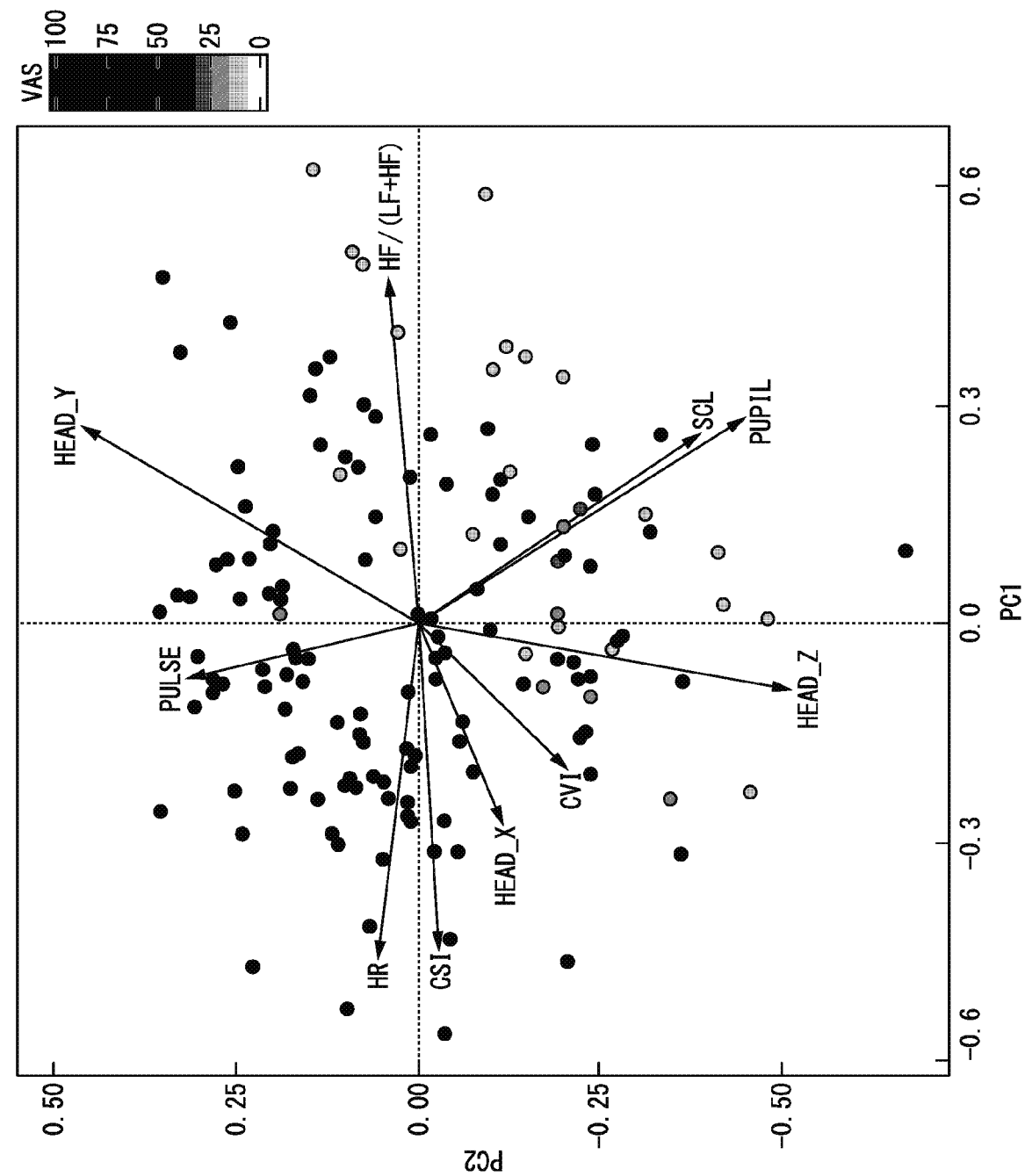
FIG. 8 is a diagram illustrating a principal component analysis result of a feature value according to the embodiment.

FIG. 8 illustrates an example of a PCA result of a feature value. In the PCA, generally, an eigenvector norm of a feature value having great contribution and serving as a principal feature value is largest, and an eigenvector norm of a substitute feature value is smaller than that. As illustrated in FIG. 8, PUPIL and SCR are located in the substantially same vector direction, and the eigenvector norm 'PUPIL' of PUPL is larger than the eigenvector norm |SCR| of SCR. Therefore, PUPIL is used as a principal feature value, and SCR is used as a substitute feature value. In a case where a vector of a feature value in a PCA space is used, coefficient $\alpha_1$ is set to $(|PUPIL|/|SCR|)\alpha_0$.

A contribution ratio of each feature value may be calculated by using the random forest. By using the contribution ratio, the coefficient $\alpha_1$ may be set to ((contribution ratio of PUPIL)/(contribution ratio of SCL))$\alpha_0$.

According to the above-described embodiment, arousal or drowsiness can be estimated by using a feature value obtained from physiological data. Thus, data is supplemented even physiological data is temporarily defective, or a feature obtained from separate physiological data is replaced with a defective feature value to be used such that estimation can be continued. Therefore, even in a case where a data defect is generated, it is possible to continuously estimate an arousal state of a person with high accuracy while avoiding a situation such as abnormality of an extracted feature value or impossible evaluation.

For example, apparatuses acquiring physiological data used to estimate an arousal state includes cameras, various sensors, and the like. Various sensors or the like being attached to a person is complex, and motion of the person is restricted, but a camera can acquire physiological data without being attached to a person. However, in a case where the camera is used, physiological data may not be temporarily acquired due to a change in an angle or a position with respect to a measurement target, and a change in ambient light.

Therefore, an arousal state is estimated by mainly using physiological data that can be acquired by the camera, and, in a case where the physiological data cannot be acquired, the arousal state can be continuously estimated by using physiological data acquired by other apparatuses.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An arousal state estimation apparatus comprising:
   a feature value acquisition unit acquiring a plurality of types of feature values regarding an arousal state of a human body from physiological data obtained by measuring the human body; and
   an estimation unit estimating the arousal state of the human body by using principal feature values, wherein the principal feature values are some types among the plurality of types of feature values,
   wherein, in a case where one of the principal feature values is unacquirable due to a defect of the physiological data, the estimation unit estimates the arousal state of the human body by using a substitute feature value instead of the unacquirable principal feature value, wherein the substitute feature value is a different type of feature value than the principal feature values among the plurality of types of feature values acquired by the feature value acquisition unit.

2. The arousal state estimation apparatus according to claim 1,
   wherein the estimation unit uses a type of substitute feature value having a high correlation with the unacquirable principal feature value instead of the unacquirable principal feature value.

3. The arousal state estimation apparatus according to claim 2,
   wherein the physiological data includes a measurement result of a heart, respiration, a fingertip pulse, a skin resistance, blinking, a pupil, or head movement.

4. The arousal state estimation apparatus according to claim 3,
   wherein, in a case where there is a defect in the physiological data, the feature amount acquisition unit supplements the physiological data obtained at a timing related to the defect based on the physiological data obtained at another timing.

5. The arousal state estimation apparatus according to claim 2,
wherein, in a case where there is a defect in the physiological data, the feature amount acquisition unit supplements the physiological data obtained at a timing related to the defect based on the physiological data obtained at another timing.

6. The arousal state estimation apparatus according to claim 1,
wherein the physiological data includes a measurement result of a heart, respiration, a fingertip pulse, a skin resistance, blinking, a pupil, or head movement.

7. The arousal state estimation apparatus according to claim 1,
wherein, in a case where there is a defect in the physiological data, the feature amount acquisition unit supplements the physiological data at a timing related to the defect based on the physiological data obtained at another timing.

8. An arousal state estimation method comprising:

acquiring a plurality of types of feature values regarding an arousal state of a human body from physiological data obtained by measuring the human body;

estimating the arousal state of the human body by using principal feature values, wherein the principal feature values are some types among the plurality of types of feature values; and estimating, in a case where one of the principal feature values is unacquirable due to a defect of the physiological data, the arousal state of the human body by using a substitute feature value instead of the unacquirable principal feature value, wherein the substitute feature value is a different type of feature values than the principal feature value among the plurality of types of acquired feature values.

* * * * *